(12) United States Patent
Ambati

(10) Patent No.: US 8,957,035 B2
(45) Date of Patent: Feb. 17, 2015

(54) TOLL LIKE RECEPTOR (TLR) STIMULATION FOR OCULAR ANGIOGENESIS AND MACULAR DEGENERATION

(75) Inventor: Jayakrishna Ambati, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 1087 days.

(21) Appl. No.: 12/304,450

(22) PCT Filed: May 15, 2007

(86) PCT No.: PCT/US2007/011718
§ 371 (c)(1),
(2), (4) Date: Jun. 3, 2009

(87) PCT Pub. No.: WO2007/133800
PCT Pub. Date: Nov. 22, 2007

(65) Prior Publication Data
US 2009/0238793 A1    Sep. 24, 2009

Related U.S. Application Data

(60) Provisional application No. 60/800,742, filed on May 15, 2006.

(51) Int. Cl.
*A61K 48/00*     (2006.01)
*C07H 21/02*     (2006.01)
*C07H 21/04*     (2006.01)

(52) U.S. Cl.
USPC .......................... 514/44; 536/23.1; 536/24.5

(58) Field of Classification Search
CPC ............. A61K 2300/00; C12N 15/117; C12N 2310/17
See application file for complete search history.

(56) References Cited

U.S. PATENT DOCUMENTS

| 4,172,124 | A | 10/1979 | Koprowski et al. |
| 4,816,397 | A | 3/1989 | Boss et al. |
| 4,816,567 | A | 3/1989 | Cabilly et al. |
| 4,946,778 | A | 8/1990 | Ladner et al. |
| 5,225,539 | A | 7/1993 | Winter |
| 2004/0018176 | A1* | 1/2004 | Tolentino et al. ......... 424/93.21 |
| 2005/0054590 | A1 | 3/2005 | Averett |
| 2005/0119273 | A1 | 6/2005 | Lipford et al. |
| 2005/0197312 | A1 | 9/2005 | Fitzgerald et al. |

FOREIGN PATENT DOCUMENTS

| EP | 0 120 694 A2 | 10/1984 |
| EP | 0 125 023 A1 | 11/1984 |
| EP | 0 194 276 B1 | 9/1986 |
| EP | 0 239 400 A2 | 9/1987 |
| WO | WO 86/01533 A1 | 3/1986 |
| WO | WO 20-06/014653 | 2/2006 |

OTHER PUBLICATIONS

Pinhal-Enfield et al. An angiogenic switch in macrophages involving synergy between Toll-like receptors 2, 4, 7, and 9 and adenosine A(2A) receptors. Am J Pathol. 163(2):711-21, 2003.*
Alexopoulou et al., Recognition of double-stranded RNA and activation of NF-kappaB by Toll-like receptor 3, Nature 413(6857):732-8, 2001.*
Kohler et al., "Continuous Cultures of Fused Cells Secreting Antibody of Predefined Specificity", Aug. 7, 1975, pp. 495-497, vol. 256.
G. Koehler et al., "Derivation of Specific Antibody-Producing Tissue Culture and Tumor Lines by Cell Fusion", Eur. J. Immunol., 1976, pp. 511-519, vol. 6.
Milstein et al., "Antibodies to Major Histocompatibility Antigens Produced by Hybrid Cell Lines", Nature, Apr. 7, 1977, pp. 550-552, vol. 266.
Roland Newman et al., ""Primatization" of Recombinant Antibodies for Immunotherapy of Human Diseases: A Macaque/ Human Chimeric Antibody Against Human CD4", Biotechnology, Nov. 1992, pp. 1455-1460, vol. 10.
Robert E. Bird et al., "Single-Chain Antigen-Binding Proteins", Science, Oct. 21, 1988, pp. 423-426, vol. 242, No. 4877, American Association for the Advancement of Science.
International Search Report dated Feb. 21, 2008 (One (1) page).
Adam J. Karpala et al., "Immune Responses to dsRNA: Implications for Gene Silencing Technologies", Immunology and Cell Biology, 2005, pp. 211-216, vol. 83, 2005 Australasian Society for Immunology, Inc.
Peter A. Campochiaro et al., "Retinal and Choroidal Neovascularization", Journal of Cellular Physiology, Apr. 4, 2000, pp. 301-310, vol. 184, 2000 Wiley-Liss, Inc.
Raghu Kalluri et al., "Generic Block on Angiogenesis", Nature, Apr. 3, 2008, pp. 543 and 545, vol. 452, 2008 Nature Publishing Group.
Kathy Aschheim et al., "Research Highlights", Nature Biotechnology, May 2008, p. 530, vol. 26, No. 5, 2008 Nature Publishing Group.
"Wandering Eye for RNAi", Nature Medicine, Community Corner, Jun. 2008, p. 611, vol. 14, No. 6, 2008 Nature Publishing Group (http://www.nature.com/naturemedicine).
Mark E. Kleinman et al., "Sequence- and Target-Independent Angiogenesis Suppression by siRNA Via $TLR_3$," Nature (International Weekly Journal of Science), Apr. 3, 2008, pp. 591-597, vol. 452.
Andrew Pollack, "Study is Setback for Some RNA-Based Drugs", The New York Times, Business, Apr. 2, 2008.
Examiner's First Report dated Mar. 14, 2012 from corresponding AU Application 2007249698.

* cited by examiner

*Primary Examiner* — Amy Bowman
(74) *Attorney, Agent, or Firm* — Crowell & Moring LLP

(57) ABSTRACT

Provided are methods and compositions for the treatment or prevention of ocular angiogenesis and neovascularization. Administration of stimulators of the TLR3 and TLR7 receptors, Trif or of IL-10 and IL-12 inhibits ocular angiogenesis. Furthermore, all siRNAs (both targeted and non-targeted) can inhibit ocular angiogenesis.

14 Claims, 20 Drawing Sheets

TOLL LIKE RECEPTOR (TLR) STIMULATION FOR OCULAR ANGIOGENESIS AND MACULAR DEGENERATION

CONTINUING APPLICATION DATA

This application claims benefit of U.S. Provisional Application No. 60/800,742, filed May 15, 2006, which is incorporated herein by reference in its entirety.

FIELD OF THE INVENTION

The present invention relates to the suppression of ocular angiogenesis by stimulation of toll-like receptor (TLR) action.

DESCRIPTION OF THE RELATED ART

The macula is the part of the retina which is responsible for central vision. Age-related macular degeneration is a chronic eye disease that occurs when tissue in the macula deteriorates. Macular degeneration affects central vision, but not peripheral vision. Macular degeneration is the leading cause of severe vision loss in people age 60 and older.

There are two forms of age-related macular degeneration: dry and wet. Dry macular degeneration is the most common type of macular degeneration and occurs when cells of the macula slowly begin to break down. Yellow deposits called "drusen" form under the retina between the retinal pigmented epithelium (RPE) and Bruch's membrane, which supports the retina. The drusen deposits are debris associated with compromised cell metabolism in the RPE. Eventually there is a deterioration of the macular regions associated with the drusen deposits resulting in a loss of central vision.

Wet macular degeneration occurs when abnormal blood vessels grow behind the macula. These vessels are fragile and can leak fluid and blood, which result in scarring of the macula and raise the potential for rapid, severe damage. Bruch's membrane breaks down, usually near drusen deposits. This is where new blood vessel growth, or neovascularization, occurs. Central vision can become distorted or lost entirely in a short period of time, sometimes within days. Wet macular degeneration is responsible for about 10 percent of the cases of age-related macular degeneration, but it accounts for about 90 percent of the cases of legal blindness.

SUMMARY OF THE INVENTION

The present invention relates to a method of inhibiting ocular angiogenesis. In one aspect the method comprises exposing a retinal or choroidal cell to a toll-like receptor-stimulatory effective amount of a compound which stimulates the activity of a toll-like receptor, including TLR3 and/or TLR7. In another aspect the method comprises exposing a retinal or choroidal cell to an effective amount of IL-10 and/or IL-12 and/or IFN-γ.

The present invention also relates to a composition for the inhibition of ocular angiogenesis. In one aspect, the composition comprises a compound which stimulates the activity of TLR3 and/or TLR7 and/or Trif. In another aspect, the composition comprises IL-10 and/or IL-12 and/or IFN-γ.

The invention also relates to a method for screening for a compound that interacts with TLR3 or TLR7 or Trif. In one aspect, the method comprises contacting TLR3 or TLR7 or Trif polypeptide or binding fragment thereof with a test compound, and determining if a complex is formed between TLR3 or TLR7 or Trif polypeptide or binding fragment thereof and the test compound. In another aspect, the test compound identified as interacting with TLR3 or TLR7 or Trif is assayed for the ability to inhibit ocular angiogenesis.

Other systems, methods, features and advantages of the present invention will be or become apparent to one with skill in the art upon examination of the following drawings and detailed description. It is intended that all such additional systems, methods, features and advantages be included within this description, be within the scope of the present invention, and be protected by the accompanying claims.

DESCRIPTION OF PREFERRED EMBODIMENTS

Figure 1:
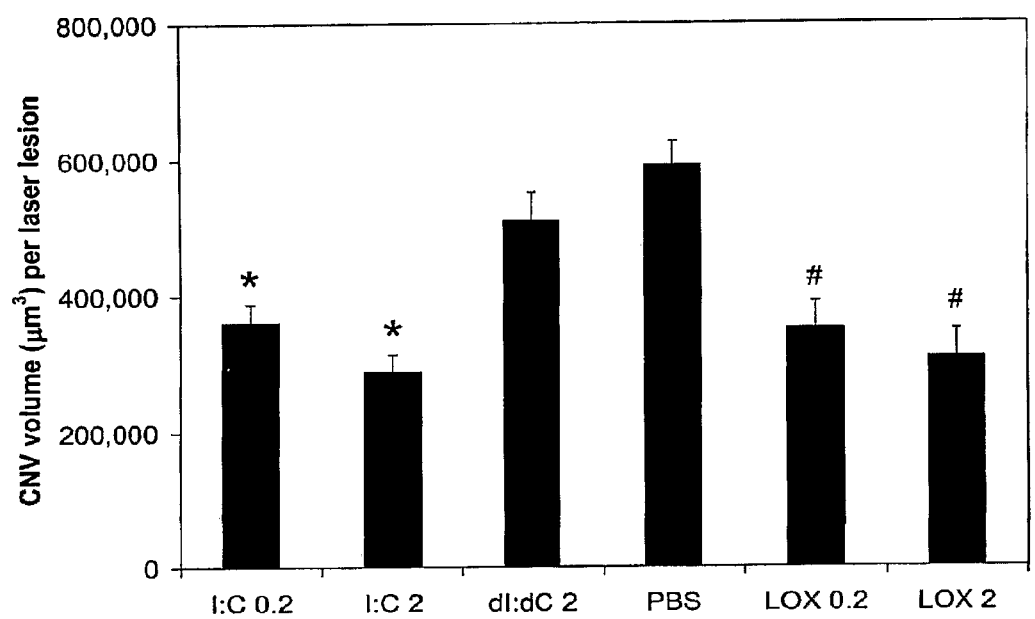
FIG. 1 illustrates the effect of poly I:C, poly dI:dC and loxoribine on choroidal neovascularization.

Toll-like receptors (TLRs) are type I transmembrane proteins involved in innate immunity by recognizing microbial conserved structures. Toll-like receptors can help activate the adaptive immune response, thereby linking innate and acquired immune responses. Ten TLRs (named TLR1 to TLR10) have been identified in humans, with each TLR being specific for a different microbial-associated molecular pattern. The present inventor has surprisingly found that stimulation of TLR3 and/or TLR7 and/or Trif (the adapter protein for TLR3) can inhibit ocular angiogenesis.

The invention relates to methods and compositions for the treatment or prevention of ocular angiogenesis and neovascularization. Administration of stimulators of the TLR3 and/or TLR7 inhibits ocular angiogenesis. In addition, administration of stimulators of Trif, the adapter protein for TLR3, inhibits ocular angiogenesis. Ocular angiogenesis includes choroidal angiogenesis and retinal angiogenesis. Compositions and methods for stimulating TLR3 and/or TLR7 and/or Trif for the treatment and/or prevention of neovascular disease are provided. Also provided are novel therapeutic targets and diagnostic markers for choroidal neovascularization.

Any compound which stimulates the activity of TLR3 and/or TLR7 and/or Trif may be used in the present invention. Such compounds include stimulatory molecules which bind directly to TLR3 and/or TLR7 and/or Trif, such as a TLR3 agonist or TLR7 agonist or Trif agonist, respectively, or an antibody which binds to and activates the TLR3 or TLR7 receptor or Trif.

Natural agonists for TLR3 include viral double-stranded RNA. Any natural agonist of TLR3 can be used to stimulate TLR3 activity according to the present invention. In addition, other ligands can also be used to stimulate TLR3 activity. Such ligands include sequence-specific (or targeted) and sequence-nonspecific (or non-targeted) double stranded RNA. The double stranded RNA can be an siRNA, or any other double stranded RNA.

Although not intending to bound by any theory or mechanism of action as to how double stranded RNA stimulates TLR3 activity, the present inventors have observed that double stranded RNA appears to act on the exterior of the cell surface when stimulating TLR3 activity. In particular, double stranded RNA appears to activate cell surface TLR3 in order to inhibit ocular angiogenesis, rather than working via RNA interference inside the cell as is generally presumed. Hence, embodiments of the present invention include methods of inhibiting ocular angiogenesis, such as choroidal neovascularization, by activation of cell surface TLR3 via double stranded RNA, including a siRNA.

The siRNAs for use in the present invention are designed according to standard methods in the field of RNA interference. Introduction of siRNAs into cells may be by transfection with expression vectors, by transfection with synthetic dsRNA, or by any other appropriate method. Transfection with expression vectors is preferred.

The expression vectors which can be used to deliver siRNA according to the invention include retroviral, adenoviral and lentiviral vectors. The expression vector includes a sequence which codes for a portion of a target gene or any other sequence whether specific for a particular gene or a nonsense sequence. The gene sequence is designed such that, upon transcription in the transfected host, the RNA sequence forms a hairpin structure due to the presence of self-complementary bases. Processing within the cell removes the loop resulting in formation of a siRNA duplex. The double stranded RNA sequence should be less than 30 nucleotide bases; preferably the dsRNA sequence is 19-25 bases in length; more preferably the dsRNA sequence is 20 nucleotides in length.

The expression vectors may include one or more promoter regions to enhance synthesis of the target gene sequence. Promoters which can be used include CMV promoter, SV40 promoter, promoter of mouse U6 gene, and promoter of human H1 gene.

One or more selection markers may be included to facilitate transfection with the expression vector. The selection marker may be included within the expression vector, or may be introduced on a separate genetic element. For example, the bacterial hygromycin B phosphotransferase gene may be used as a selection marker, with cells being grown in the presence of hygromycin to select for those cells transfected with the aforementioned gene.

Synthetic dsRNA may also be introduced into cells to provide gene silencing by siRNA. The synthetic dsRNAs are less than 30 base pairs in length. Preferably the synthetic dsRNAs are 19-25 base pairs in length. More preferably the dsRNAs are 19, 20 or 21 base pairs in length, optionally with 2-nucleotide 3' overhangs. In other embodiments, the synthetic dsRNAs may be 5, 7, 9 or 11 base pairs in length, optionally with 2-nucleotide 3' overhangs. The 3' overhangs are preferably TT residues. Synthetic dsRNAs may be naked dsRNA, or dsRNA containing one or more 2-O'-methyl groups.

Synthetic dsRNAs can be introduced into cells by injection, by complexing with agents such as cationic lipids, by use of a gene gun, or by any other appropriate method.

Stimulators of TLR7-function include imiquimod (R-837), resiquimod (R-848), loxoribine, and bropirimine. There are also reports of single-stranded RNA or viral RNA functioning as ligands, and therefore stimulators, of TLR7 function. Any of these stimulators of TLR7 function can be used according to the present invention.

Additional compounds for stimulating TLR3 and/or TLR7 and/or Trif include antibodies which specifically bind TLR3 or TLR7 or Trif.

The antibodies of the present invention can be polyclonal or monoclonal, and the term antibody is intended to encompass both polyclonal and monoclonal antibodies. Antibodies of the present invention can be raised against an appropriate immunogen, including proteins or polypeptides of the present invention, such as isolated and/or recombinant mammalian TLR3 or TLR7 or Trif or portion thereof, or synthetic molecules, such as synthetic peptides.

Preparation of immunizing antigen, and polyclonal and monoclonal antibody production can be performed using any suitable technique. A variety of methods have been described (see e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) are isolated using selective culture conditions, and cloned by limiting dilution. Cells which produce antibodies with the desired specificity are selected by a suitable assay (e.g., ELISA).

Single chain antibodies, and chimeric, humanized or primatized (CDR-grafted) antibodies, as well as chimeric or CDR-grafted single chain antibodies, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023. B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single chain antibodies.

In addition, functional fragments of antibodies, including fragments of chimeric, humanized, primatized or single chain antibodies, can also be produced. Functional fragments of foregoing antibodies retain at least one binding function and/or modulation function of the full-length antibody from which they are derived. For example, antibody fragments capable of binding to a mammalian TLR3 or TLR7 or Trif or portion thereof, including, but not limited to, Fv, Fab, Fab' and F(ab').sub.2 fragments are encompassed by the invention. Such fragments can be produced by enzymatic cleavage or by recombinant techniques. For instance, papain or pepsin cleavage can generate Fab or F(ab').sub.2 fragments, respectively. Alternatively, antibodies can be produced in a variety of truncated forms using antibody genes in which one or more stop codons has been introduced upstream of the natural stop site. For example, a chimeric gene encoding a F(ab').sub.2 heavy chain portion can be designed to include DNA sequences encoding the CH.sub.1 domain and hinge region of the heavy chain.

Anti-idiotypic antibodies are also provided. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See e.g., U.S. Pat. No. 4,699,880. Single chain, and chimeric, humanized or primatized (CDR-grafted), as well as chimeric or CDR-grafted single chain anti-idiotypic antibodies can be prepared, and are encompassed by the term anti-idiotypic antibody. Antibody fragments of such antibodies can also be prepared.

The present inventor has also found that inhibition of ocular angiogenesis by stimulation of TLR3 and/or TLR7 and/or Trif is mediated, at least in part, by IL10 and/or IL12. Thus, ocular angiogenesis can also be inhibited by administration of IL10 and/or IL12 to a subject in need thereof. The methods described herein for administration of stimulators of TLR3 and/or TLR7 and/or Trif are also generally applicable to the administration of IL10 and/or IL12 to inhibit ocular angiogenesis.

Modulation of mammalian TLR3 or TLR7 or Trif function according to the present invention, through the stimulation of at least one function characteristic of a mammalian TLR3 or TLR7 or Trif, provides an effective and selective way of inhibiting ocular angiogenesis. One or more stimulators of TLR3 and/or TLR7 and/or Trif, such as those identified as described herein, can be used to inhibit ocular angiogenesis for therapeutic purposes.

Thus, the present invention provides a method of inhibiting ocular angiogenesis in an individual in need of such therapy, comprising administering a compound which stimulates TLR3 or TLR7 or Trif function to an individual in need of such therapy. Such individuals include those having age-related macular degeneration.

The methods of the present invention can be used in any mammalian species, including human, monkey, cow, sheep, pig, goat, horse, mouse, rat, dog, cat, rabbit, guinea pig, hamster and horse. Humans are preferred.

According to the method of the invention, one or more compounds can be administered to the host by an appropriate route, either alone or in combination with another drug. An effective amount of a compound is administered. An effective amount is an amount sufficient to achieve the desired therapeutic effect, under the conditions of administration, such as an amount sufficient for stimulation of TLR3 and/or TLR7 and/or Trif function, and thereby inhibition of ocular angiogenesis.

A variety of routes of administration are possible including, but not necessarily limited to oral, dietary, topical, parenteral (e.g., intravenous, intraarterial, intramuscular, subcutaneous injection), inhalation (e.g., intrabronchial, intranasal or oral inhalation, intranasal drops), and intraocular injection routes of administration, depending on the disease or condition to be treated. Intraocular injection routes include periocular (subconjunctival/transscleral), intravitreous, subretinal and intracameral modes of injection.

Formulation of a compound to be administered will vary according to the route of administration selected (e.g., solution, emulsion, capsule). An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, Remington's Pharmaceutical Science, 16th Edition, Mack, Ed. 1980). For inhalation, the compound is solubilized and loaded into a suitable dispenser for administration (e.g., an atomizer, nebulizer or pressurized aerosol dispenser). As another example, a compound may be administered via a sustained release device or composition which is implanted in the vitreous humor, aqueous humor, on the sclera, in the sclera, in the suprachoroidal space, or in the subretinal space.

In another embodiment, the present invention provides methods for screening compounds that interact with TLR3 and/or TLR7 and/or Trif. The present invention is useful for screening compounds by using TLR3 or TLR7 or Trif polypeptide or binding fragments thereof in any of a variety of drug screening techniques. The TLR3 or TLR7 or Trif polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between TLR3 or TLR7 or Trif and the agent being tested. Alternatively, one can examine the diminution in complex formation between TLR3 or TLR7 or Trif and its target cell, monocyte, etc. caused by the agent being tested.

Thus, the present invention provides methods of screening for drugs or any other agents which can affect ocular angiogenesis and disease. These methods comprise contacting such an agent with a TLR3 or TLR7 or Trif polypeptide or fragment thereof and assaying (i) for the presence of a complex between the agent and the TLR3 or TLR7 or Trif polypeptide or fragment, or (ii) for the presence of a complex between the TLR3 or TLR7 or Trif polypeptide or fragment and the cell, by methods well known in the art. In such competitive binding assays, the TLR3 or TLR7 or Trif polypeptide or fragment is typically labeled. After suitable incubation, free TLR3 or TLR7 or Trif polypeptide or fragment is separated from that present in bound form, and the amount of free or uncomplexed label is a measure of the ability of the particular agent to bind to TLR3 or TLR7 or Trif or to interfere with the TLR3 or TLR7 or Trif and agent complex.

Another technique for drug screening provides high throughput screening for compounds having suitable binding affinity to the TLR3 or TLR7 or Trif polypeptide and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with TLR3 or TLR7 or Trif polypeptide and washed. Bound TLR3 or TLR7 or Trif polypeptide is then detected by methods well known in the art. Purified TLR3 or TLR7 or Trif can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding TLR3 or TLR7 or Trif specifically compete with a test compound for binding to TLR3 or TLR7 or Trif polypeptides or fragments thereof. In this manner, the antibodies can be used to detect the presence of any peptide which shares one or more antigenic determinants with TLR3 or TLR7 or Trif.

The present invention also contemplates the use of drug screening assays in which drugs or any other agents are monitored in a bioassay, such as the ability of the drug or agent to inhibit ocular angiogenesis. Such a drug screening assay may be used in conjunction with the various binding assays described above, i.e., drugs or other agents may be first tested for their ability to bind to TLR3 or TLR7 or Trif, and those compounds having binding affinity for TLR3 or TLR7 or Trif are then tested in a bioassay, such as the ability of the drug or agent to inhibit ocular angiogenesis. Alternatively, the bioassay may be conducted with the drug or agent with or without a compound which blocks the action of TLR3 or TLR7 or Trif, such as an antibody against TLR3 or TLR7 or Trif. Inhibition of ocular angiogenesis with the drug or agent but no inhibition of ocular angiogenesis with drug or agent in the presence of a compound which blocks the action of TLR3 or TLR7 or Trif would be indicative of a compound that inhibits ocular angiogenesis by interacting with TLR3 or TLR7 or Trif. Similar screening assays can be performed comparing ocular angiogenesis in wild-type cells versus cells in which the genes for TLR3 or TLR7 or Trif are knocked out, with inhibition of ocular angiogenesis in wild-type cells due to exposure to drug agent and no inhibition in the knockout cells being indicative of the drug or agent inhibiting ocular angiogenesis by interacting with TLR3 or TLR7 or Trif.

EXAMPLE 1

Animals

All animal experiments were in accordance with the guidelines of the University of Kentucky IACUC and the Association for Research in Vision and Ophthalmology. Male C57BL/6J mice (Jackson Laboratory) between 6 and 8 weeks of age were used to minimize variability. The sources for the other mouse strains were: TLR3−/−, IL-10−/−, IL-12−/−, IFNγ−/− (Jackson Laboratory), IFNAR-1−/− (gift of H. Virgin, Washington University), TLR7−/− (gift of D. Golenback, University of Massachusetts), TLR9−/− (gift of E. Pearlman, Case Western Reserve University), VEGFR1 tyrosine kinase−/− (gift of M. Shibuya, University of Tokyo), Trif−/− (Trif deficient Lps2 mice from The Jackson Laboratories). For all procedures, anesthesia was achieved by intraperitoneal injection of 50 mg/kg ketamine hydrochloride (Ft. Dodge Animal Health) and 10 mg/kg xylazine (Phoenix Scientific), and pupils were dilated with topical 1% tropicamide (Alcon Laboratories).

CNV

Laser photocoagulation (532 nm, 200 mW, 100 ms, 75 μm) (OcuLight GL, Iridex Corporation) was performed (volume studies: 3/eye; protein analyses/flow cytometry: 12/eye) on both eyes of each animal to induce CNV (choroidal neovascularization). CNV volumes were measured by scanning laser confocal microscope (TCS SP, Leica) with 0.5% FITC-*Griffonia simplicifolia* Isolectin B4 (Vector Laboratories) or 0.5% FITC-rat antibody against mouse CD31 (BD Biosciences). Volumes obtained by lectin and CD31 staining were highly correlated ($r^2$=0.95).

Drugs and Injections

Loxoribine (Invivogen), poly I:C (Invivogen), poly dI:dC (Sigma-Aldrich), IFNγ (eBioscience), rat antibodies against mouse IL-10 (R&D Systems), IL-12 (eBioscience), or IL-23 (eBioscience), control rat IgG (Serotec), siRNAs (Dharmacon) against GFP, BGLAP2, CDH16, SFTPB, 3 nonsense targets (NS1, NS2 and NS3) with at least 4 base mismatch to all known mouse genes, 2-O'-methyl NS2, an siRNA that does not enter the RISC complex, an siRNA against VEGF-A (Bevasiranib; with sense strand having the sequence ACCU-CACCAAGGCCAGCACdTdT, and the antisense strand having the sequence GUGCUGGCCUUGGUGAGGUdTdT), and an siRNA against VEGFR-1 (Sirna-027; with the sense strand having the sequence CUGAGUUUAAAAGGCAC-CCdTdT, and the antisense strand having the sequence GGGUGCCUUUUAAACUCAGdTdT) were injected into the vitreous humor of mice using a 33-gauge double-caliber needle (Ito Corporation) immediately after laser injury. Also tested were shorter non-targeted siRNAs: a 5+2 length nucleotide (5 nucleotides plus a 2 nucleotide overhang, with one strand having the sequence UAAGGdTdT and the other strand having the sequence CCUUAdTdT), and a 11+2 length nucleotide (11 nucleotides plus a 2 nucleotide overhang, with one strand having the sequence UCAUAGCCUUAdTdT and the other strand having the sequence UAAGGC-UAUGAdTdT).

ELISA

IL-10 and IL-12 protein levels were measured by ELISA (Peprotech) according to the manufacturer's instructions, as were IFN-α, IFN-β and IFN-γ (PBL InterferonSource). Total protein was measured according to Biorad.

Statistics

Because the probability of each laser lesion developing CNV is influenced by the group to which it belongs, the mouse, the eye, and the laser spot, the mean lesion volumes were compared using a linear mixed model with a split plot repeated measures design. The whole plot factor was the genetic group to which the animal belonged while the split plot factor was the eye. Statistical significance was determined at the 0.05 level. Post hoc comparison of means was constructed with a Bonferroni adjustment for multiple comparisons. ELISA measurements were compared by Student's t-test.

Results

FIG. 1 illustrates the effect of poly I:C, poly dI:dC and loxoribine on choroidal neovascularization. Poly I:C, a toll like receptor (TLR)3 ligand, reduced CNV compared to the control poly dI:dC, which does not activate TLR3, in a dose-dependent fashion (0.2-2 μg) *P<0.05; n=16. Loxoribine, a TLR7 ligand, reduced CNV compared to the control PBS in a dose-dependent fashion (0.2-2 μg) #P<0.05; n=16.

Figure 2:
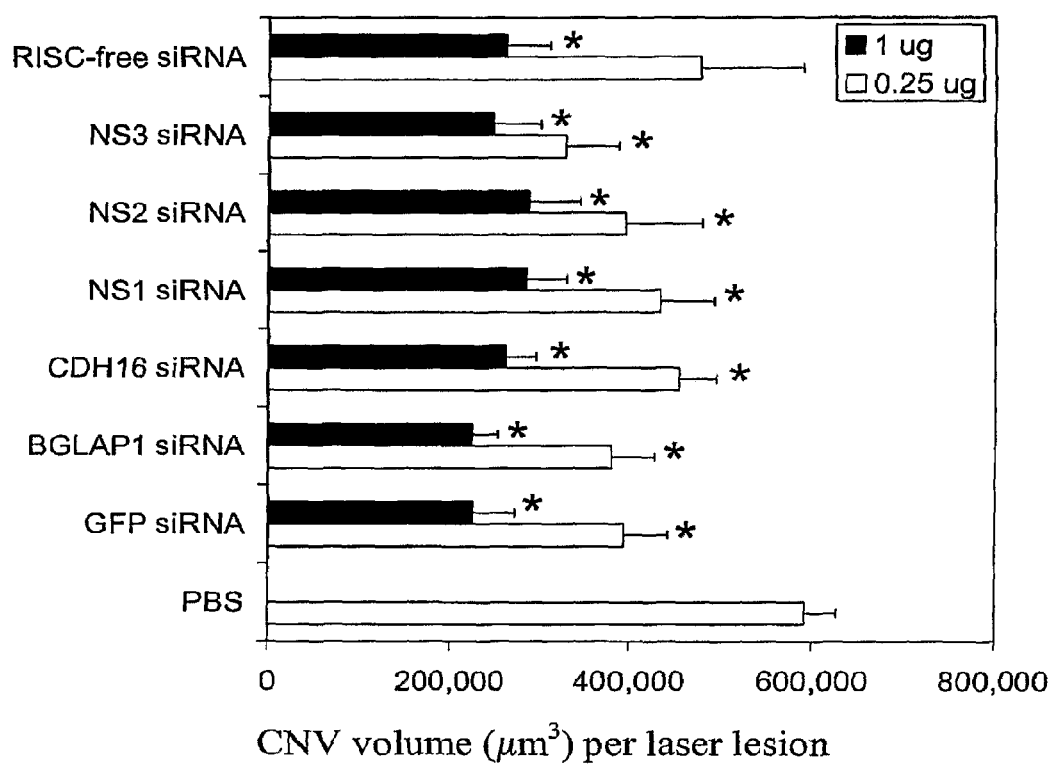
FIG. 2 shows the effect of various siRNAs on choroidal neovascularization.

FIG. 2 shows the effect of various siRNAs on choroidal neovascularization. siRNA against green fluorescent protein (GFP), bone gamma carboxyglutamate protein 1 (BGLAP1—bone specific), cadherin 16 (CDH16—kidney specific), and 3 different nonsense (NS) siRNAs not matching any sequence in the genome, and an siRNA that does not enter the RISC complex (RISC-free) all reduced CNV in a dose-dependent fashion. *P<0.05, n=12-16. This demonstrates that any siRNA, including those targeted to random sequences, to non-mammalian sequences, and to genes not expressed in the eye, can suppress CNV.

Figure 3:
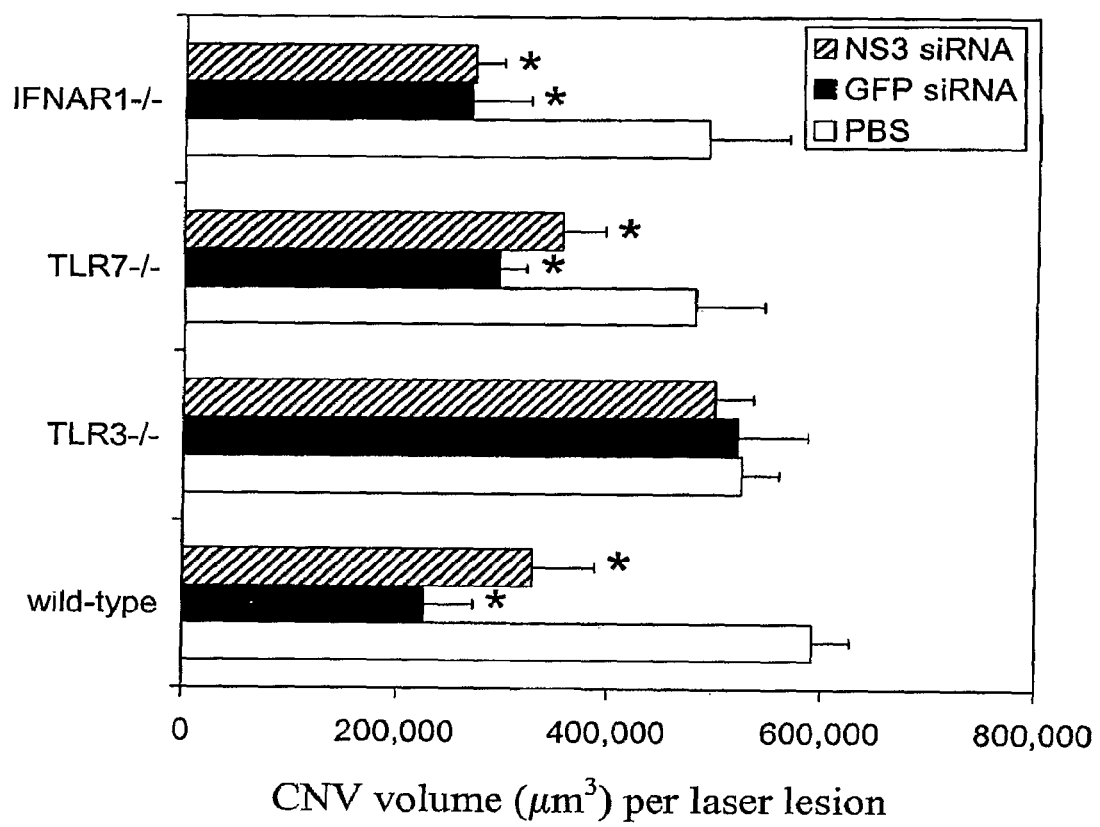
FIG. 3 illustrates the effect of various siRNAs on choroidal neovascularization in wild-type, TLR3−/−, TLR7−/−, and interferon receptor (IFNAR1)−/− mice.

FIG. 3 illustrates the effect of various siRNAs on choroidal neovascularization in wild-type, TLR3−/−, TLR7−/−, and interferon receptor (IFNAR1)−/− mice. 1 μg of siRNA against green fluorescent protein (GFP), or a nonsense sequence siRNA (NS3) both reduced CNV in wild-type, TLR7−/−, and interferon receptor (IFNAR1)−/− mice. However, they did not reduce CNV in TLR3−/− mice, indicating that the "non-specific/generic" suppression of CNV is mediated via TLR3 and not via TLR7 or via induction of interferon. N=8-16.

Figure 4:
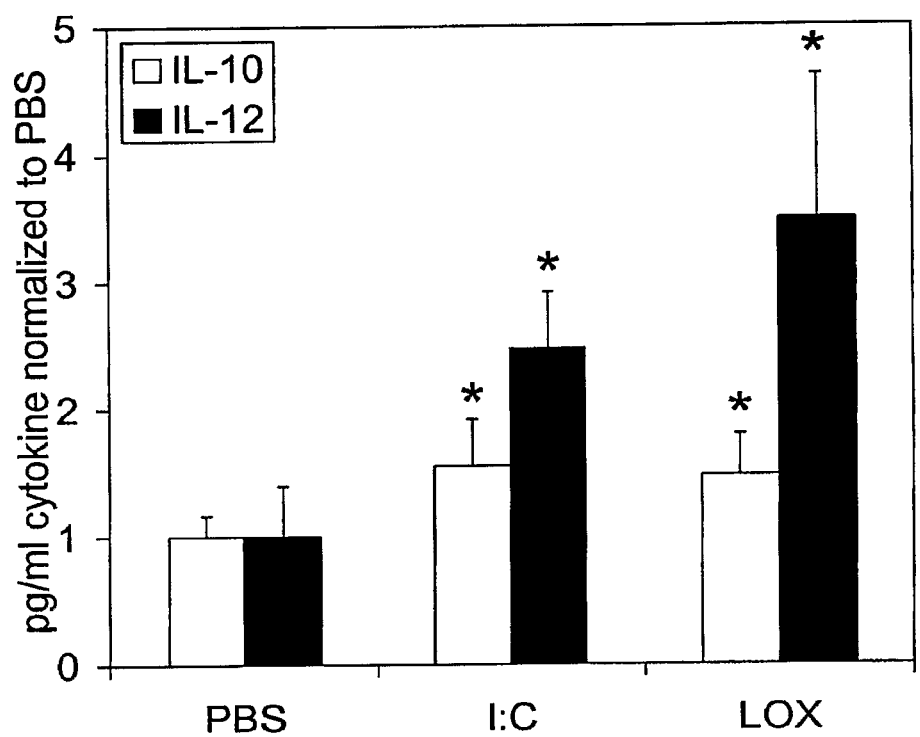
FIG. 4 shows the effect of poly I:C and loxoribine on IL-10 and IL-12 production in the RPE/choroid of wild-type mice.

FIG. 4 shows the effect of poly I:C and loxoribine on IL-10 and IL-12 production in the RPE/choroid of wild-type mice. 2 μg of poly I: C, a TLR3 ligand, and loxoribine (LOX), a TLR7 ligand, induced IL-12 and IL-10 protein expression in the RPE/choroid of wild-type mice at 1 and 3 days after laser injury, respectively. N=12.

Figure 5:
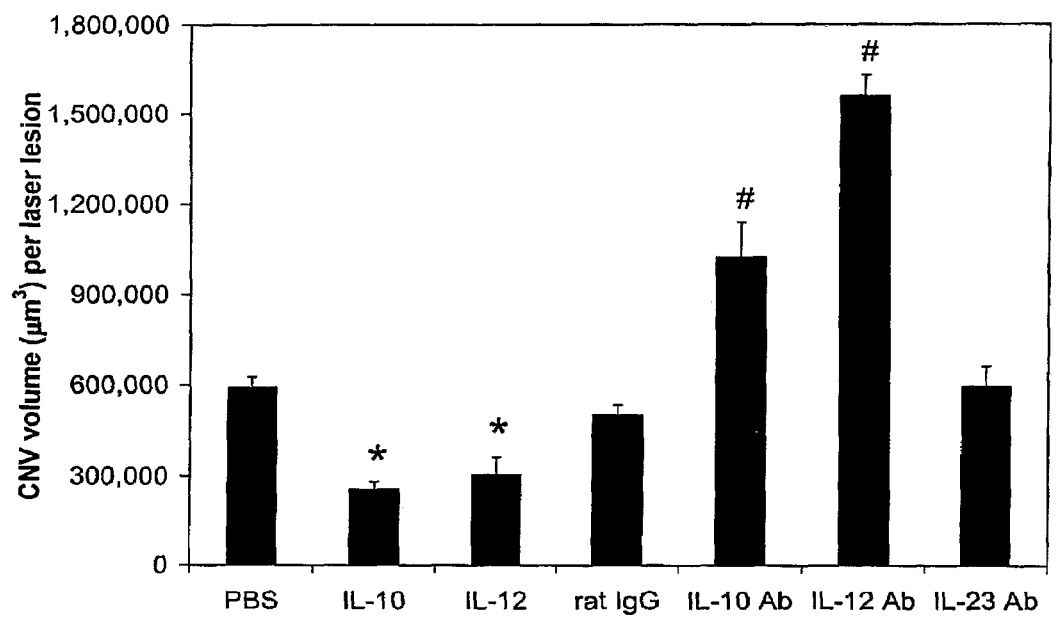
FIG. 5 illustrates the effect of IL-10 and IL-12 on choroidal neovascularization.

FIG. 5 illustrates the effect of IL-10 and IL-12 on choroidal neovascularization. IL-10 and IL-12 both (1 ng) reduced CNV compared to PBS (*P<0.05), and neutralizing antibodies (Ab) against IL-10 (1 μg) or IL-12 (150 ng) both increased CNV compared to isotype control rat IgG. The IL-12 Ab also can inhibit IL-23; however, IL-23 Ab (150 ng) did not affect CNV. n=8-16.

Figure 6:
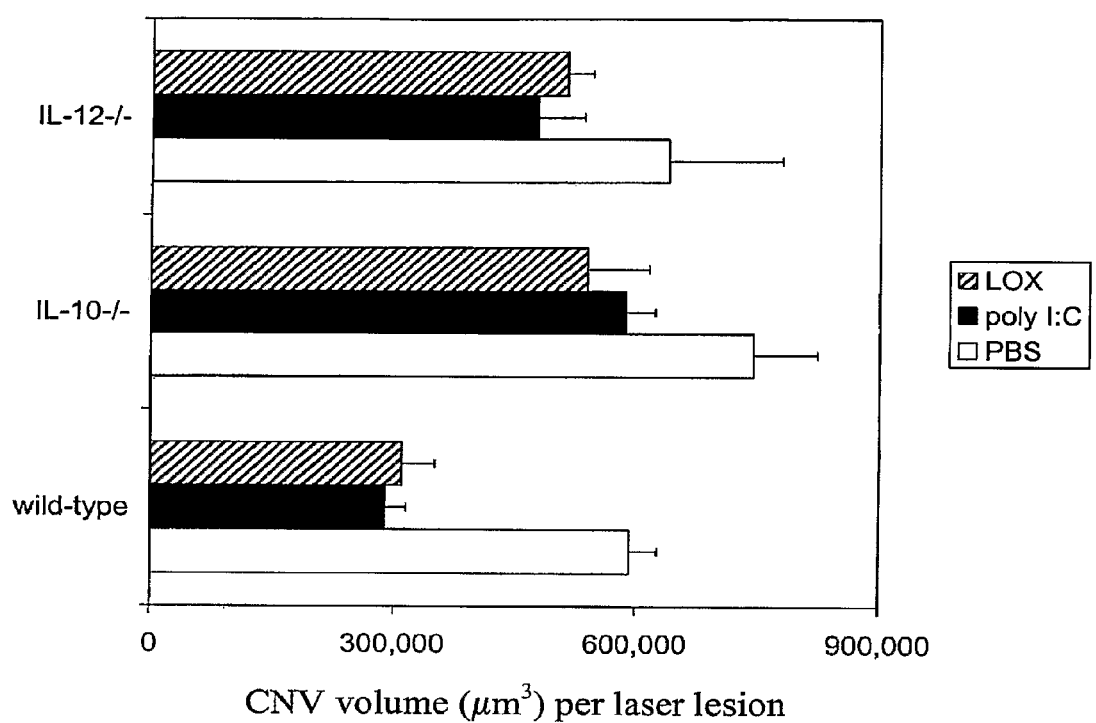
FIG. 6 shows the effect of poly I:C and loxoribine on choroidal neovascularization in wild-type, IL10−/− and IL12−/− mice.

FIG. 6 shows the effect of poly I:C and loxoribine on choroidal neovascularization in wild-type, IL10−/− and IL12−/− mice. The ability of poly I:C and loxoribine (both 2 μg) to suppress CNV is markedly reduced in IL-10−/− and IL-12−/− mice, indicating that the anti-angiogenic effects of these two TLR ligands are mediated in large part via IL-10 and IL-12. n=12.

Figure 7:
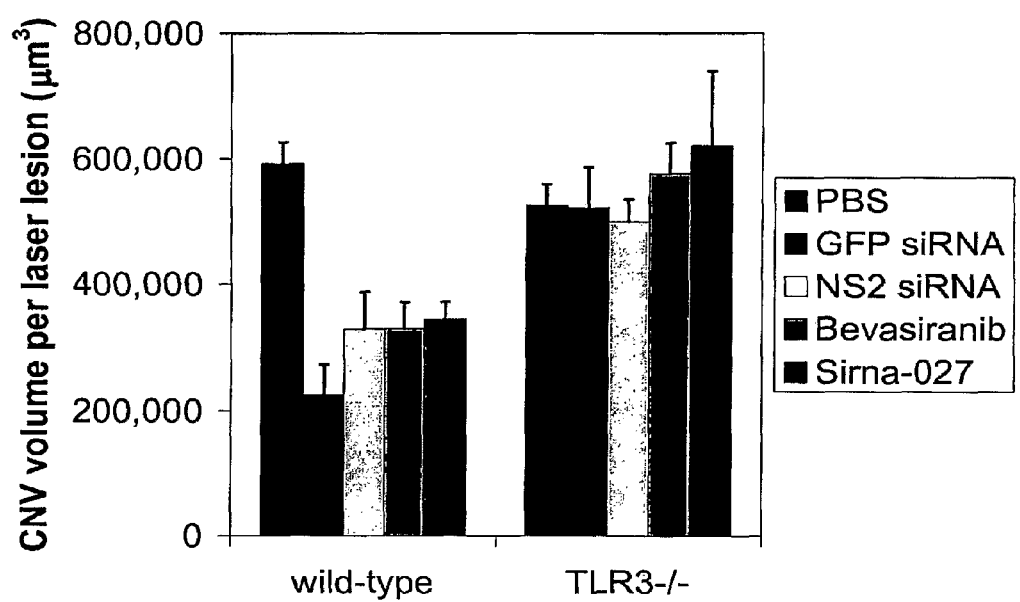
FIG. 7 shows the effect of non-targeted and targeted siRNAs on choroidal neovascularization in wild type and TLR3−/− mice.

FIG. 7 shows the effect of non-targeted and targeted siRNAs on choroidal neovascularization in wild type and TLR3−/− mice. Non-targeted siRNA (GFP siRNA and NS2 siRNA) and targeted siRNA (Bevasiranib, siRNA against VEGF-A; and Sirna-027, siRNA against VEGFR-1) were all essentially equally effective in suppressing CNV in wild-type mice, while non of them suppressed CNV in TLR3−/− mice (The Jackson Laboratories). Hence, both non-targeted and targeted siRNA appear to function via TLR3 in modulating CNV. All siRNAs were injected at 0.25 μg into the vitreous humor immediately after laser injury. All CNV volumes in wild-type mice injected with siRNAs were significantly lower than PBS injected CNV volume (*P<0.05). In TLR3−/− mice, all differences were not statistically significant.

Figure 8:
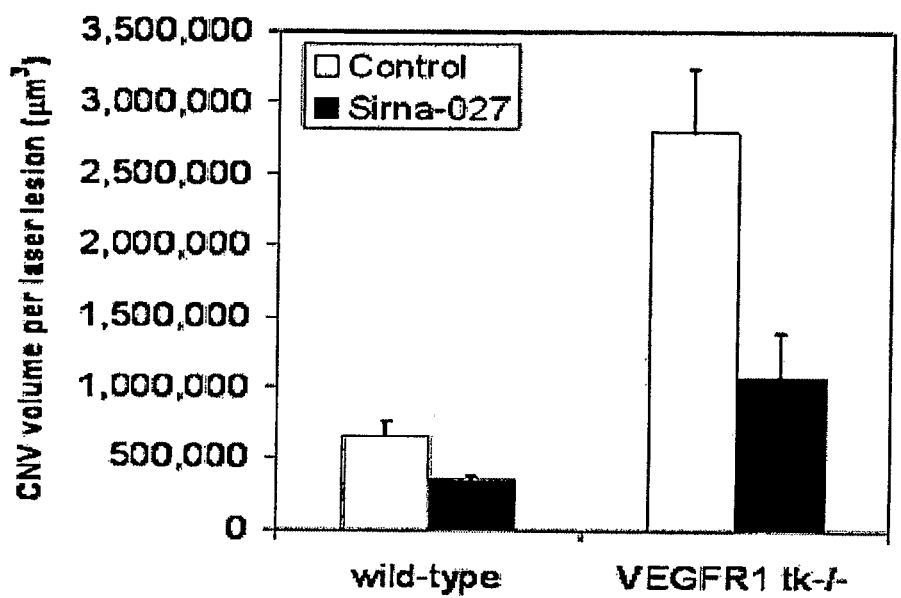
FIG. 8 illustrates the effect of Sirna-027 (siRNA against VEGFR1) on choroidal neovascularization in VEFGR1 tyrosine kinase−/− mice.

FIG. 8 illustrates the effect of Sirna-027 (siRNA against VEGFR1) on choroidal neovascularization in VEFGR1 tyrosine kinase−/− mice. Sirna-027 suppressed CNV in VEGFR1 tk−/− mice. These mice are deficient in VEGFR1 signaling and, therefore, the results demonstrate that "targeted" siRNAs function even in the absence of the target's endogenous functional nucleic acid. siRNA-027 was injected at 0.25 μg into the vitreous humor immediately after laser injury. CNV volumes in eyes injected with Sirna-027 were significantly lower than control (PBS) injected eyes both in wild-type and VEGFR1 tk−/− mice (P<0.05).

Figure 9:
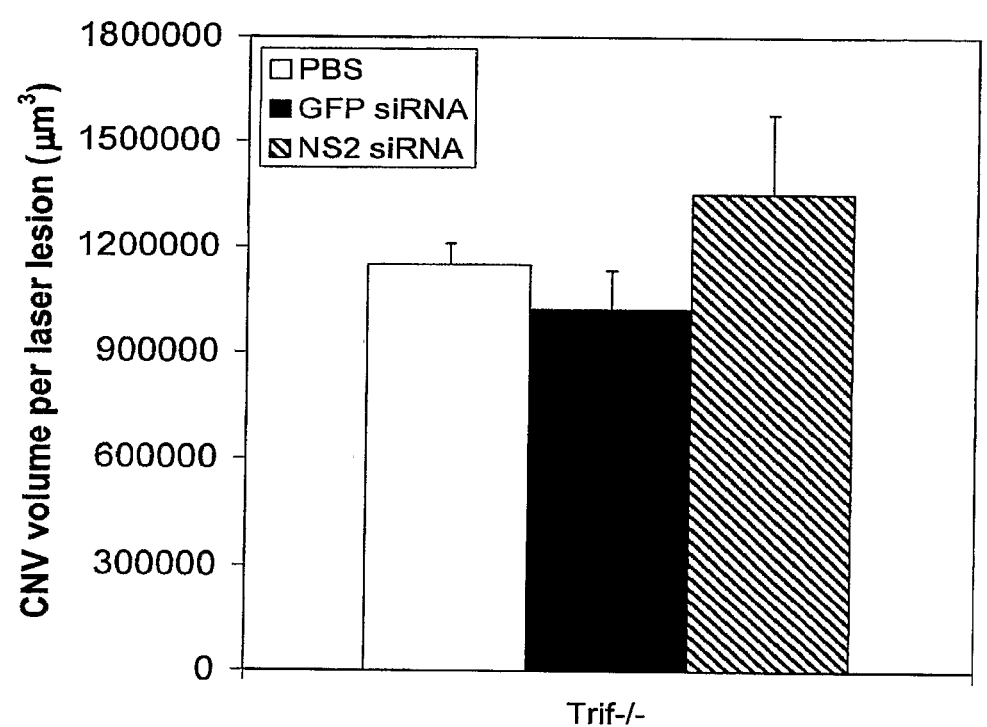
FIG. 9 shows that non-targeted siRNA suppression of CNV is abolished in mice deficient in Trif (Toll/IL-1 receptor domain-containing adaptor-inducing IFN-β; Toll/interleukin-1 receptor/resistance (TIR) adaptor protein).

FIG. 9 shows that non-targeted siRNA suppression of CNV is abolished in mice deficient in Trif (Toll/IL-1 receptor domain-containing adaptor-inducing IFN-β; Toll/interleukin-1 receptor/resistance (TIR) adaptor protein). Trif is the adaptor protein for TLR3; thus, the results confirm that siRNA functions via TLR3 and Trif signaling. All siRNAs were injected at 1 μg into the vitreous humor immediately after laser injury. All differences not statistically significant.

Figure 10:
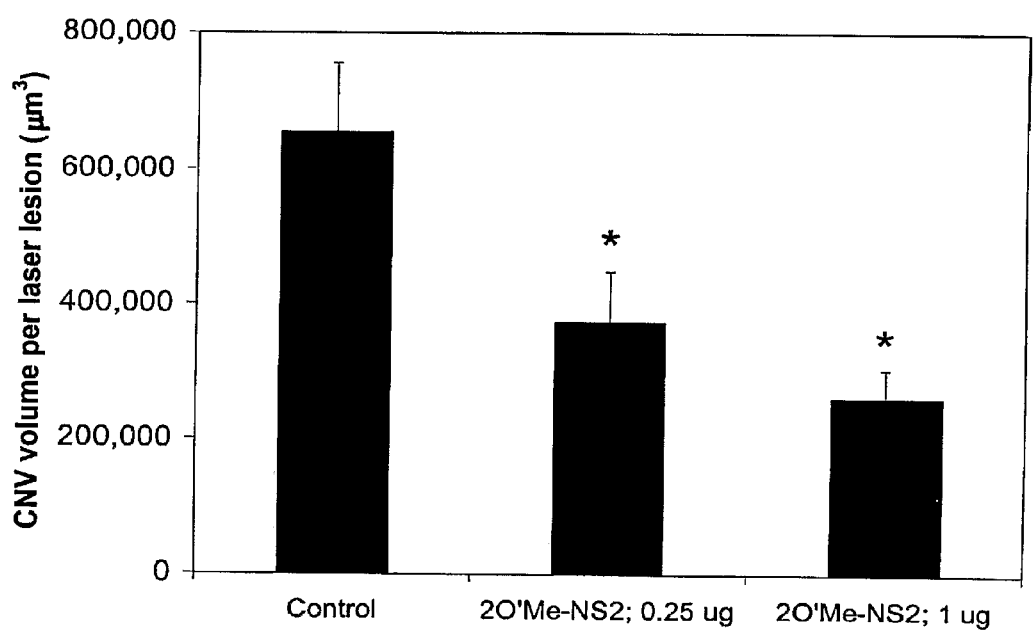
FIG. 10 illustrates that 2-O'-methyl modified non-targeted siRNA retains its ability to suppress CNV when administered intravitreously.
Figure 11:
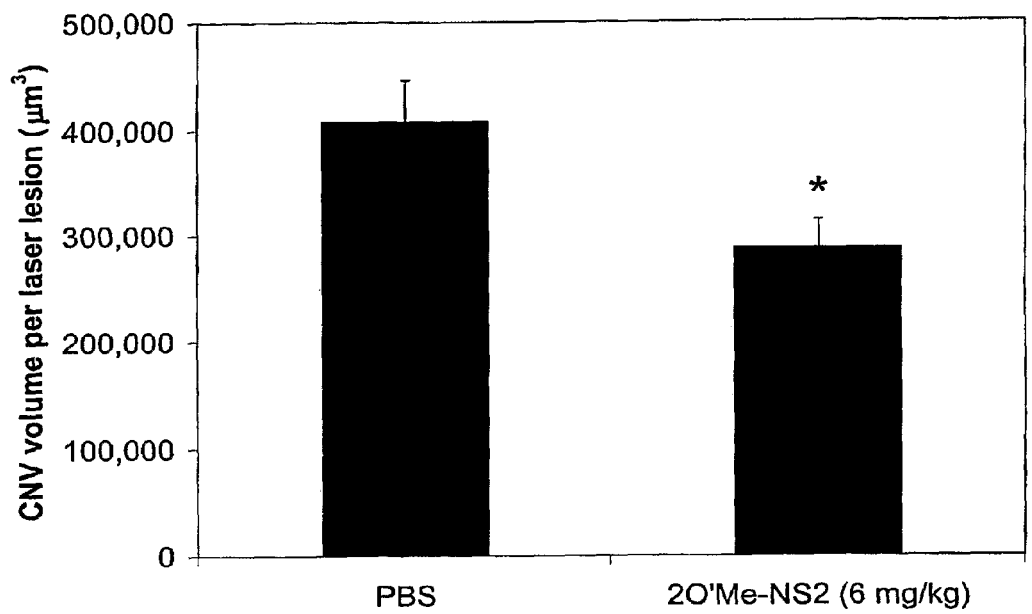
FIG. 11 shows that 2-O'-methyl modified non-targeted siRNA retains its ability to suppress CNV when administered intraperitoneally.

FIG. 10 illustrates that non-targeted siRNA (NS2) modified with 2-O'-methyl groups on alternate bases retains the ability to suppress choroidal neovascularization when administered intravitreously. siRNA was injected into the vitreous humor immediately after laser injury. *P<0.05. FIG. 11 shows that 2-O'-methyl modified non-targeted siRNA retains its ability to suppress CNV when administered intraperitoneally.

Figure 12:
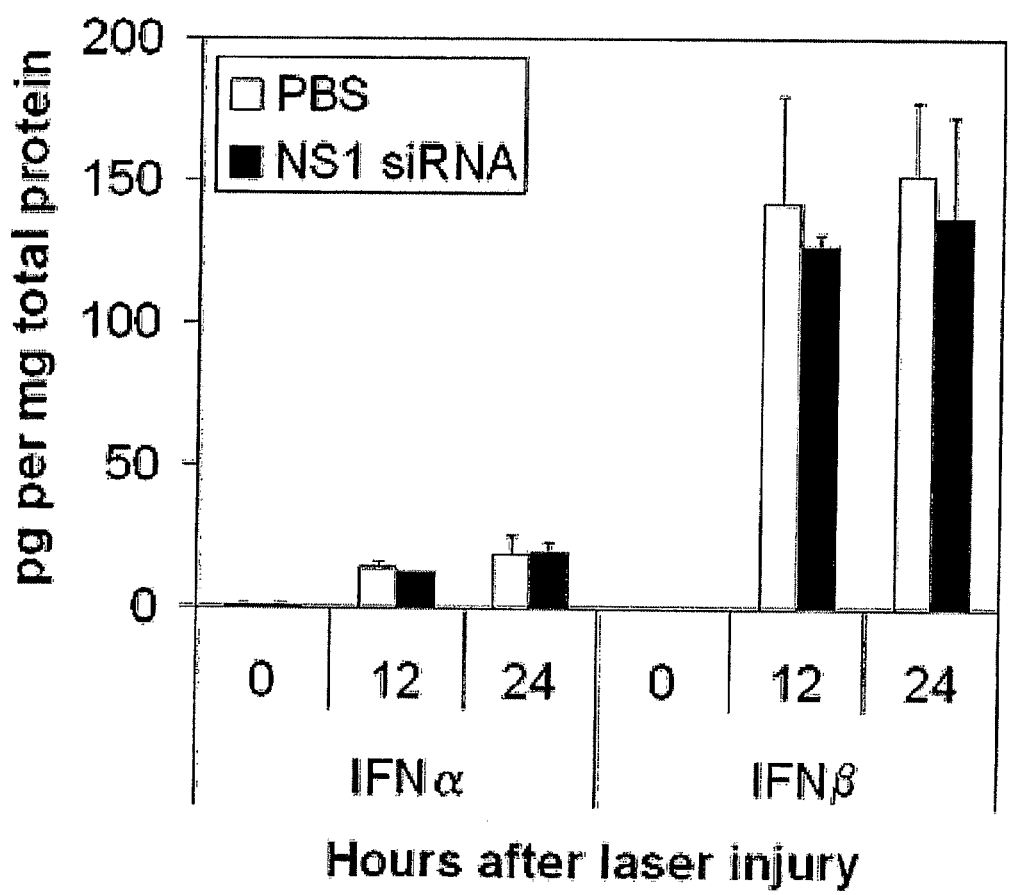
FIG. 12 shows that non-targeted siRNA (NS1 siRNA) does not induce IFN-α or IFN-β in retinal pigmented epithelium/choroid of mice after laser injury.
Figure 13:
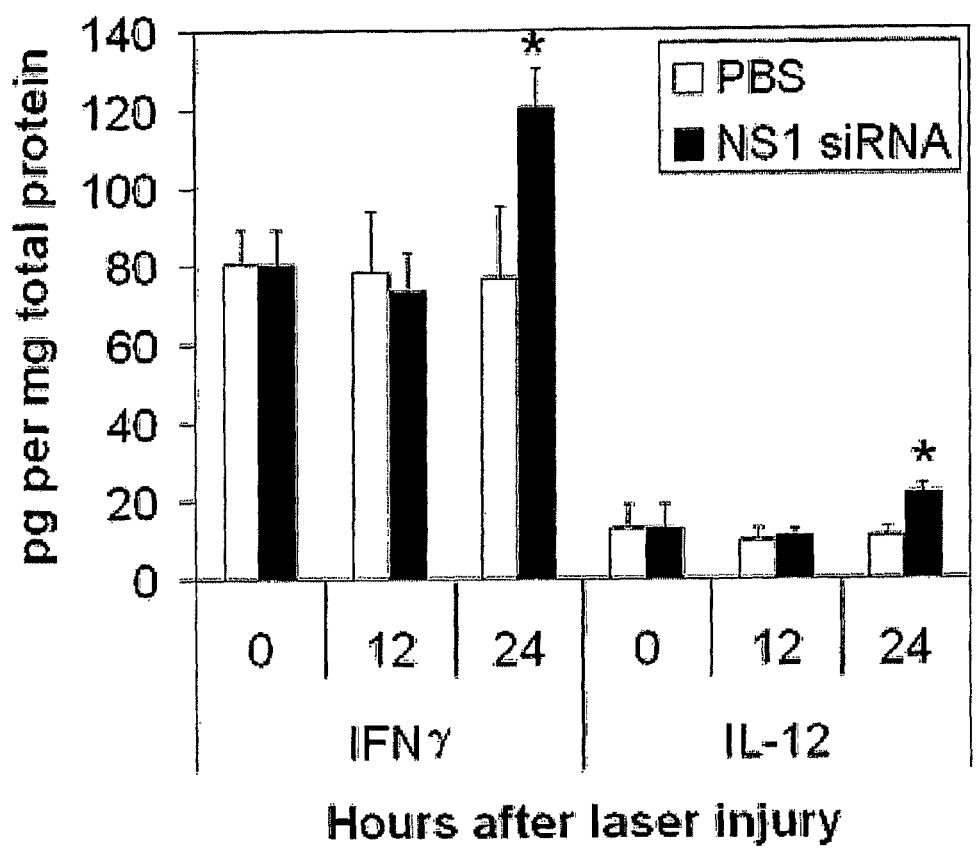
FIG. 13 illustrates that non-targeted siRNA (NS1 siRNA) induces IFN-γ and IL-12 in retinal pigmented epithelium/choroid of mice after laser injury.

FIG. 12 shows that non-targeted siRNA (NS1 siRNA) does not induce IFN-α or IFN-β in retinal pigmented epithelium/ choroid of mice after laser injury at the indicated times (hours). siRNA (1 μg) was injected into the vitreous humor immediately after laser injury. IFN-α and IFN-β were measured by ELISA and normalized to total protein. All differences not statistically significant. FIG. 13 illustrates that non-targeted siRNA (NS1 siRNA) induces IFN-γ and IL-12 in retinal pigmented epithelium/choroid of mice after laser injury at the indicated times (hours). siRNA (1 μg) was injected into the vitreous humor immediately after laser injury. IFN-γ was measured by ELISA (PBL Interferon-Source) and IL-12 was measured by ELISA (eBioscience) and normalized to total protein. *P<0.05.

Figure 14:
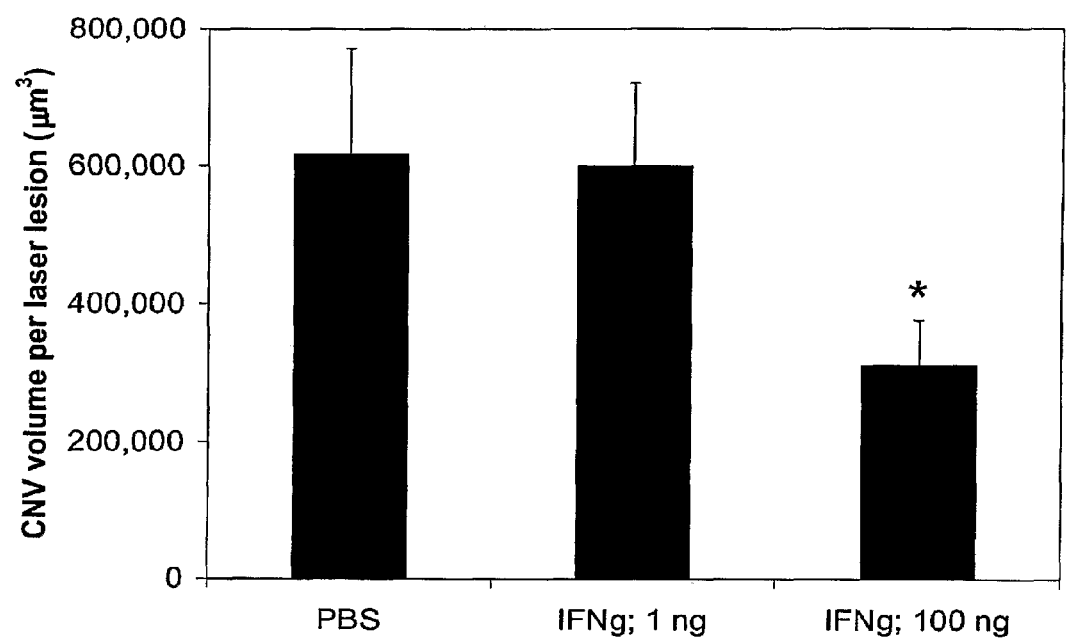
FIG. 14 shows that recombinant mouse IFNγ reduces choroidal neovascularization in mice in a dose-dependent fashion.

FIG. 14 shows that recombinant mouse IFNγ injected into the vitreous humor immediately after laser injury reduced choroidal neovascularization in wild-type C57BL/6J mice in a dose-dependent fashion. *P<0.05.

Figure 15:
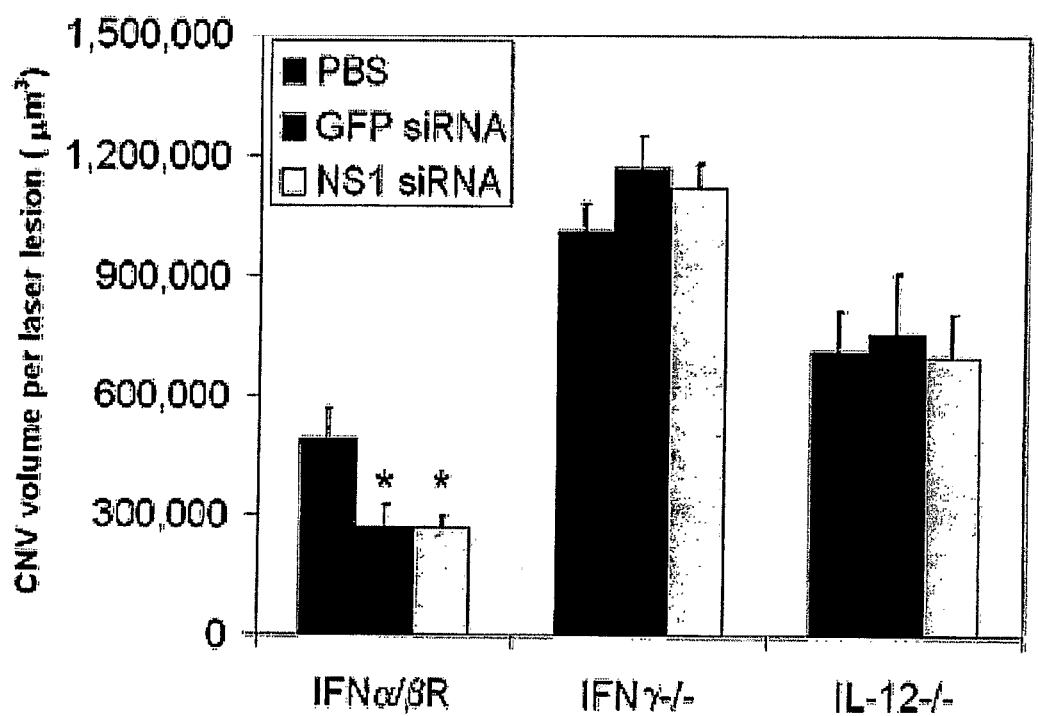
FIG. 15 illustrates that non-targeted siRNAs (GFP siRNA and NS1 siRNA) suppress choroidal neovascularization in IFNα/βR−/− mice (also known as IFNAR1−/− mice) but not in IFNγ−/− or IL12−/− mice.

FIG. 15 illustrates that non-targeted siRNAs (GFP siRNA and NS1 siRNA) (1 μg injected into the vitreous humor immediately after laser injury) suppress choroidal neovascularization in IFNα/βR−/− mice (also known as IFNAR1−/− mice) but not in IFNγ−/− or IL12−/− mice. The results indicate that non-targeted siRNAs function via IFNγ and IL12. *P<0.05.

Figure 16:
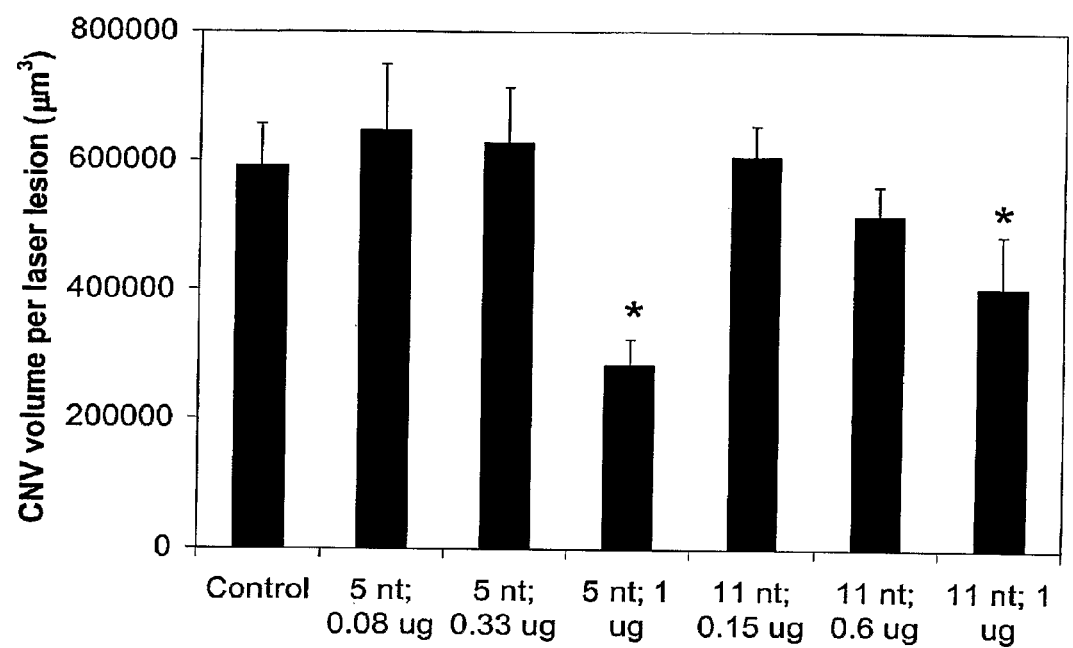
FIG. 16 shows that non-targeted siRNAs of shorter length (5+2 nucleotides and 11+2 nucleotides) also suppress laser-induced choroidal neovascularization.

FIG. 16 shows that non-targeted siRNAs of shorter length (5+2 nucleotides and 11+2 nucleotides) also suppress laser-induced choroidal neovascularization in wild-type C57BL/6J mice. *P<0.05.

Figure 17:
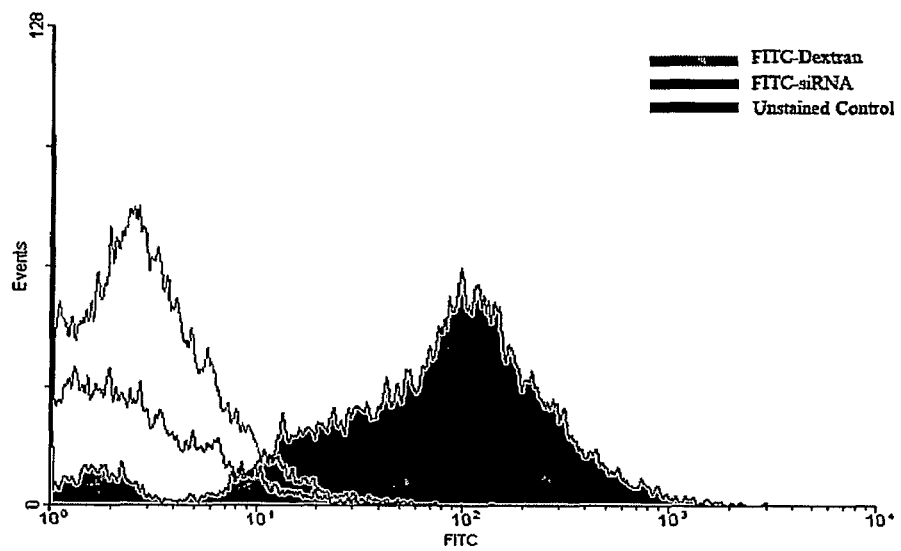
FIG. 17 illustrates flow cytometry experiments of wild-type mouse RPE/choroid cell suspensions.

FIG. 17 illustrates flow cytometry experiments of wild-type mouse RPE/choroid cell suspensions. The results reveal that, when injected into the vitreous humor, FITC-siRNA (NS2) does not enter cells (FITC-siRNA curve does not demonstrate a "right shift" compared to unstained control curve) whereas 10 kDa FITC-dextran (Sigma-Aldrich) does enter cells (FITC-Dextran curve demonstrates a "right shift"). This indicates that cellular uptake of carrier-free/naked siRNA is poor and, thus, that the biological effects of such siRNA are mediated by cell surface interactions.

Figure 18:
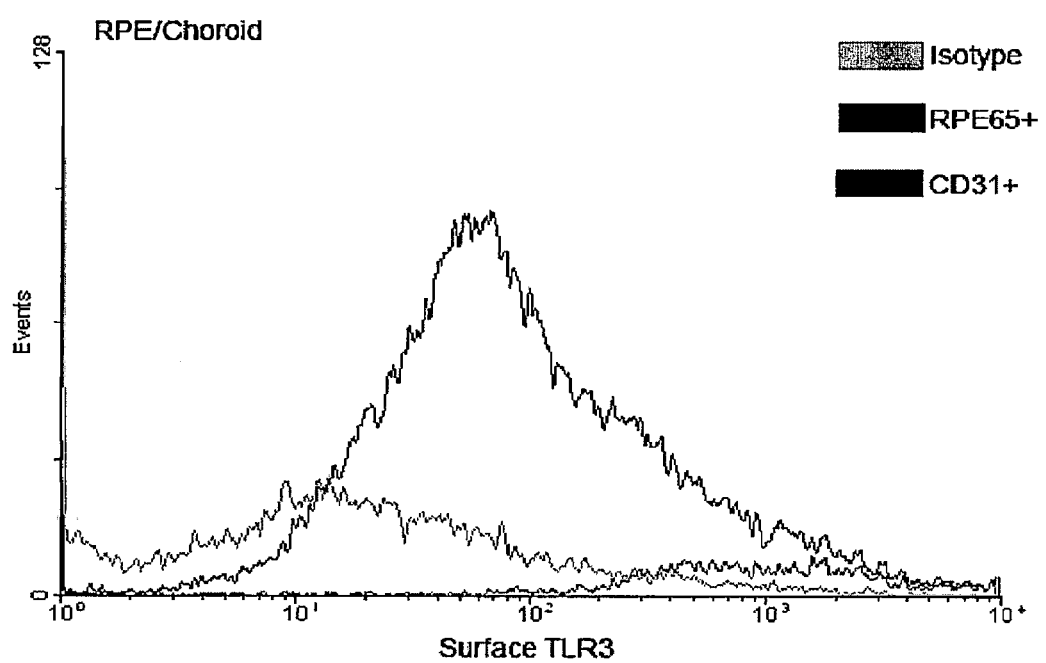
FIG. 18 shows flow cytometry experiments (performed without permeabilization) of wild-type mouse RPE/choroid cell suspensions.

FIG. 18 shows flow cytometry experiments (performed without permeabilization) of wild-type mouse RPE/choroid cell suspensions. The results reveal that TLR3 is expressed on the surface of RPE65+ (retinal pigmented epithelium) cells and CD31+ (choroidal endothelial cells), using anti-RPE65 Ab (gift of T. M Redmond, National Eye Institute), anti-CD31 Ab (BD Biosciences), and anti-TLR3 Ab (Imgenex).

Figure 19:
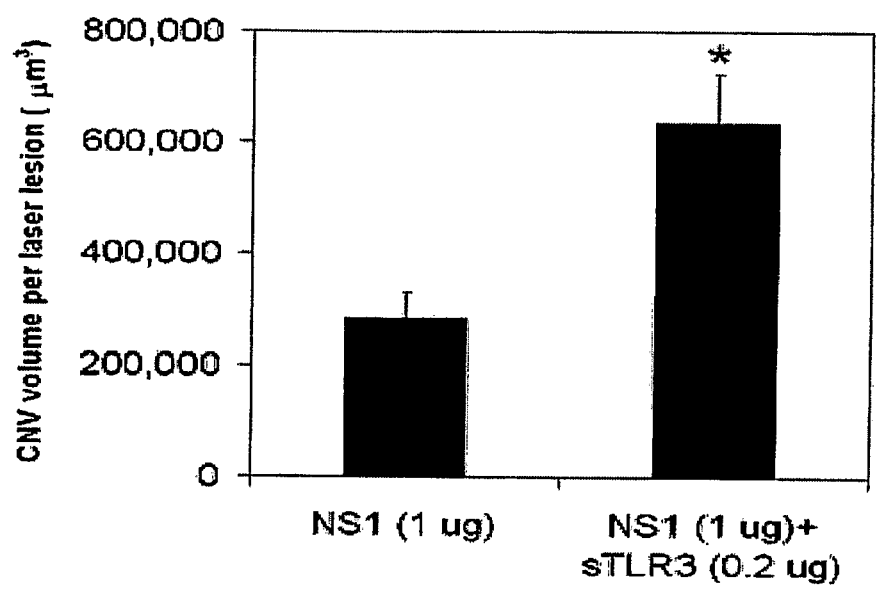
FIG. 19 illustrates that preincubation with recombinant soluble TLR3 abolished the suppression of CNV in wild-type mice by siRNA (NS1) injected into the vitreous humor immediately after laser injury.

FIG. 19 illustrates that preincubation with recombinant soluble TLR3 (R&D Systems) abolished the suppression of CNV in wild-type mice by siRNA (NS1) injected into the vitreous humor immediately after laser injury. *P<0.05. These data indicate the siRNA directly interacts with TLR3.

Figure 20:
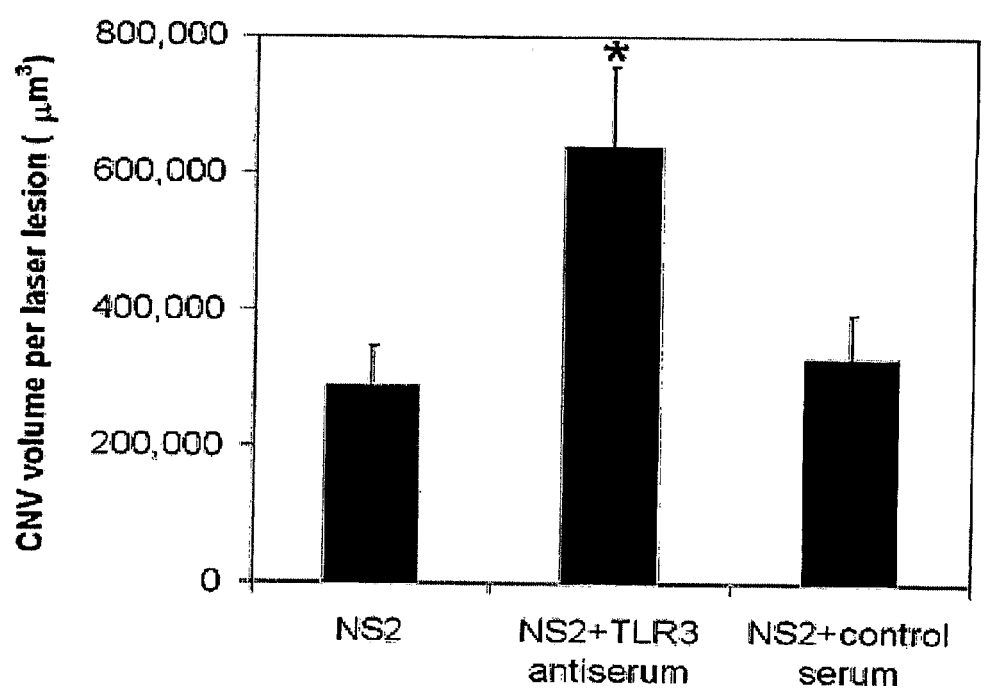
FIG. 20 shows that neutralizing rat anti-serum against mouse TLR3, but not control rat serum, abolished suppression of choroidal neovascularization in wild-type mice induced by siRNA-NS2 injected into the vitreous humor immediately after laser injury.

FIG. 20 shows that neutralizing rat anti-serum against mouse TLR3 (200 nl), but not control rat serum (200 nl), abolished suppression of choroidal neovascularization in wild-type mice induced by siRNA-NS2 (1 µg) injected into the vitreous humor immediately after laser injury. *P<0.05. Because the TLR3 antibodies would not be expected to penetrate the cell, these data indicate that siRNA activates cell surface TLR3.

All references cited in this disclosure are incorporated by reference to the same extent as if each reference had been incorporated by reference in its entirety individually.

While the invention has been described in detail and with reference to specific embodiments thereof, it will be apparent to one skilled in the art that various variations and modifications can be made therein without departing from the spirit and scope thereof. All such variations and modifications are intended to be included within the scope of this disclosure and the present invention and protected by the following claims.

I claim:

1. A method of inhibiting ocular angiogenesis comprising exposing a retinal or choroidal cell to a toll-like receptor-stimulatory effective amount of a toll-like receptor 3 agonist, which stimulates the activity of a toll-like receptor 3, and inhibits ocular angiogenesis, wherein the toll-like receptor 3 agonist is double-stranded RNA.

2. The method of claim 1 wherein the double-stranded RNA is a naked double-stranded RNA or a double-stranded RNA having an 0-methyl group at one or more 2'-positions.

3. The method of claim 1 wherein the double-stranded RNA has 19, 20 or 21 base pairs, optionally with 2-nucleotide 3' overhangs.

4. The method of claim 1 wherein the double-stranded RNA has 5, 7, 9 or 11 base pairs, optionally with 2-nucleotide 3' overhangs.

5. The method of claim 1 wherein the compound is a sequence-nonspecific double-stranded RNA.

6. The method of claim 1 wherein the compound is a sequence-specific double-stranded RNA.

7. The method of claim 1 wherein the compound is a poly I:C.

8. The method of claim 1 wherein the double-stranded RNA functions by activating cell surface TLR3.

9. The method of claim 1 wherein the choroidal cell is a choroidal endothelial cell.

10. The method of claim 1 wherein exposing the retinal or choroidal cell to the toll-like receptor-stimulatory compound takes place in a mammal.

11. The method of claim 10 wherein the compound is orally administered to the mammal.

12. The method of claim 10 wherein the compound is intravenously administered to the mammal.

13. The method of claim 10 wherein the compound is intraocularly injected into the mammal.

14. The method of claim 10, wherein the compound is administered via a sustained release device or composition which is implanted in the vitreous humor, aqueous humor, on the sclera, in the suprachoroidal space, or in the subretinal space.

* * * * *